United States Patent [19]

Short et al.

[11] 4,372,930
[45] Feb. 8, 1983

[54] ZEOLITE NU-3

[75] Inventors: Glyn D. Short, Yarm; Thomas V. Whittam, Darlington, both of England

[73] Assignee: Imperial Chemical Industries Limited, London, England

[21] Appl. No.: 260,839

[22] Filed: May 5, 1981

[30] Foreign Application Priority Data

May 13, 1980 [GB] United Kingdom ............... 8015890

[51] Int. Cl.$^3$ ...................... C01B 33/20; C01B 33/28
[52] U.S. Cl. ............................... 423/326; 252/455 Z; 423/328; 423/329; 423/332; 423/593; 423/594; 423/600; 546/10
[58] Field of Search ............................ 423/326–332, 423/593, 594, 600; 252/431 N, 455 Z; 546/2, 10, 14

[56] References Cited

U.S. PATENT DOCUMENTS 3,459,676 8/1969 Kerr ............................ 423/328 X
3,692,470 9/1972 Ciric ............................ 423/329
4,000,248 12/1976 Martin ............................ 423/329
4,076,842 2/1978 Plank et al. ..................... 423/328
4,285,922 8/1981 Audeh et al. .................... 423/328

Primary Examiner—Edward J. Meros
Attorney, Agent, or Firm—Cushman, Darby & Cushman

[57] ABSTRACT

A new zeolite material designated Nu-3 having a molar composition expressed by the formula:

0.5 to 1.5$R_2O$:$Y_2O_3$:at least 5$XO_2$:0 to 400$H_2O$ wherein R is a monovalent cation or 1/n of a cation of valency n where n is a whole number of 2 or more, X is silicon and/or germanium, Y is one or more of aluminium, iron or gallium and $H_2O$ is water of hydration additional to water notionally present when R is H, and having an X-ray diffraction pattern substantially as shown in Table 1, is prepared from a reaction mixture containing $XO_2$ (preferably silica), $Y_2O_3$ (preferably alumina) and an optionally substituted quinuclidinium ion.

17 Claims, No Drawings

ZEOLITE NU-3

The present invention relates to a novel Zeolite hereinafter referred to as zeolite Nu-3, to a method of making it and to processes using it as an adsorbent and catalyst.

According to the present invention we provide zeolite Nu-3 having a molar composition expressed by the formula:

0.5 to 1.5 $R_2O$: $Y_2O_3$: at least 5 $XO_2$: 0 to 400 $H_2O$ wherein R is a monovalent cation or $1/n$ of a cation of valency n where n is a whole number of 2 or more, X is silicon and/or germanium, Y is one or more of aluminium, iron or gallium and $H_2O$ is water of hydration additional to water notionally present when R is H, and has an X-ray diffraction pattern substantially as set out in Table 1 (as determined by standard technique using copper K$\alpha$ radiation). The X-ray pattern is affected in minor ways by the type of cation present, but there are greater changes in relative intensities on burning out organic cations. No further changes occur on preparing hydrogen forms of Nu-3.

TABLE 1

| | | | | | | | | | | | |
|---|---|---|---|---|---|---|---|---|---|---|---|
| Typical X-ray data for Zeolite Nu-3 | | | | | | | | | | | |
| dA | 11.3 | 10.1 | 8.0 | 7.65 | 6.56 | 5.71 | 5.54 | 5.09 | 4.97 | 4.75 | 4.66 | 4.61 |
| | ±0.2 | ±0.2 | ±0.14 | ±0.14 | ±0.14 | ±0.12 | ±0.10 | ±0.10 | ±0.09 | ±0.08 | ±0.08 | ±0.08 |
| I | w | w→m | m→vs | w→m | w→vs | w | w | m→vs | w | w | w | w→s |
| dA | 4.42 | 4.32 | 4.21 | 4.02 | 3.95 | 3.80 | 3.77 | 3.66 | 3.54 | 3.42 | 3.28 | 3.18 |
| | ±0.08 | ±0.08 | ±0.08 | ±0.07 | ±0.07 | ±0.07 | ±0.06 | ±0.06 | ±0.06 | ±0.06 | ±0.05 | ±0.05 |
| I | w | w→m | s→vs | vs | w | m→s | w→m | w→m | w | w→m | w→m | w |
| dA | 3.12 | 3.03 | 2.98 | 2.81 | 2.75 | 2.59 | 2.50 | 2.07 | 2.01 | 1.90 | 1.86 | |
| | ±0.05 | ±0.05 | ±0.05 | ±0.05 | ±0.05 | ±0.04 | ±0.03 | ±0.03 | ±0.03 | ±0.02 | ±0.02 | |
| I | s | w | v→m | w | m→s | w | w | w | w | w | w | | vs = 60 to 100
s = 40 to 60
m = 20 to 40
w = 0 to 20

Within the above definition of chemical composition the number of moles of $XO_2$ is typically in the range 5 to 1000 and zeolite Nu-3 appears to be most readily formed in a state of high purity when the number of moles of $XO_2$ is in the range 10 to 300, and the number of moles of $R_2O$ is in the range 0.8 to 1.5.

This definition includes both freshly prepared zeolite Nu-3 ("freshly prepared" means the product of synthesis and washing, with optional drying as hereinafter described) and also forms of it resulting from dehydration, and/or calcination, and/or ion exchange. In freshly prepared zeolite Nu-3, R may include an alkali metal cation, especially sodium, and/or ammonium and usually includes nitrogen-containing organic cations such as derivatives of quinuclidine or cationic degradation products thereof, or precursors thereof, or mixtures of such nitrogen containing compounds. These nitrogen containing cations are hereinafter referred to as Q.

Table 2 shows X-ray data for zeolite Nu-3 as freshly prepared in the sodium N-methylquinuclidinium form and Table 3 shows X-ray data for zeolite Nu-3 in calcined sodium hydrogen form.

The freshly prepared zeolite Nu-3 may also contain nitrogen-containing compounds well in excess of the 1.5 moles set out in the aforesaid definition of the composition of zeolite Nu-3 typically in the range 0.1 to 20 moles per mole of $Y_2O_3$. Since Nu-3 is a zeolite, the excess base must be physically trapped within the crystal lattice, because it is too large to escape. It is removable, for example by thermal or oxidative degradation. This physically trapped basic material does not constitute part of the composition for the purposes of the definition. Thus a zeolite Nu-3 as made typically has the following molar composition:

TABLE 2

| Zeolite Nu-3 as freshly prepared in sodium N—methylquinuclidinium form | |
|---|---|
| d(A) | 100 I/Io |
| 10.11 | 8 |
| 8.01 | 33 |
| 7.56 | 1 |
| 6.56 | 19 |
| 5.50 | 10 |
| 5.07 | 79 |
| 4.94 | 14 |
| 4.69 | 6 |
| 4.62 | 2 |
| 4.39 | 3.5 |
| 4.21 | 56 |
| 4.01 | 100 |
| 3.78 | 35 |
| 3.54 | 6 |
| 3.42 | 3 |
| 3.27 | 18 |
| 3.18 | 2 |
| 3.12 | 48 |
| 3.03 | 9 |
| 2.81 | 5 |
| 2.75 | 38 |

TABLE 3

| Zeolite Nu-3 in calcined Na-H form | |
|---|---|
| d(A) | 100 I/Io |
| 10.10 | 21 |
| 8.03 | 100 |
| 7.55 | 8 |
| 6.58 | 75 |
| 5.51 | 3 |
| 5.07 | 40 |
| 4.94 | 2 |
| 4.62 | 1 |
| 4.21 | 49 |
| 4.01 | 85 |
| 3.78 | 22 |
| 3.54 | 11 |
| 3.42 | 6 |
| 3.28 | 22 |
| 3.12 | 51 |
| 3.03 | 11 |
| 2.81 | 8 |
| 2.75 | 42 |

Thus a zeolite Nu-3 as made typically has the following molar composition:

0.3 to 1.2 $M_2O$: 0.4 to 20 Q: $Y_2O_3$: 5 to 1000 $XO_2$: 0 to 400 $H_2O$ wherein M is an alkali metal or ammonium. The number of moles of $XO_2$ is preferably in the range 10 to 300.

The $H_2O$ content of freshly prepared zeolite Nu-3 depends on the conditions in which it has been dried after synthesis.

In calcined forms of zeolite Nu-3, R may be alkali metal but includes less or no nitrogen-containing organic compounds, since these are burnt out in the presence of air or ammonia, leaving hydrogen as the other balancing cation.

Among the ion-exchanged forms of zeolite Nu-3 the ammonium ($NH_4^+$) is of importance since it can be readily converted to the hydrogen form by calcination. The hydrogen form can also be prepared directly by exchange with an acid. The hydrogen-form and forms containing metals introduced by ion exchange are described further below.

Zeolite Nu-3 is a novel zeolite with very characteristic molecular sieve properties as demonstrated by typical sorption results given in Table 4. These results pertain to sodium hydrogen Nu-3 of Example 2. These results show, that even with 30% of its cation sites filled by sodium, zeolite Nu-3 is somewhat hydrophobic i.e. it reaches equilibrium slowly with water (hydrophilic zeolites such as zeolite A or chabasite at p/po=0.25 reach 95% equilibrium within 10 minutes). An unusual feature is that all the voidage available to water is also available to n-hexane which suggests there are no cavities within the structure with access below 8 ring windows (i.e. 4.3 A). The slow uptake of n-hexane suggests that this sodium hydrogen Nu-3 has port size very close to 4.3 A.

TABLE 4

| Adsorbate | Sorption at 25° C. P/po = 0.5 | | | |
|---|---|---|---|---|
| | Kinetic* diameter $\sigma$ (A) | Time mins | wt sorbed g/100 g | Voidage available cc/100 g |
| water (P/po = 0.25) | 2.7 | 10 | 6.5 | 6.5 |
| | | 60 | 9.3 | 9.3 |
| | | 120 | 9.9 | 9.9 |
| | | 1440 | 9.9 | 9.9 |
| n-hexane | 4.3 | 10 | 1.5 | 2.3 |
| | | 60 | 4.9 | 7.4 |
| | | 120 | 5.9 | 8.9 |
| | | 1440 | 6.0 | 9.9 |
| p-xylene | 5.8 | 10 | 0.1 | 0.15 |
| | | 1440 | 0.2 | 0.3 |

*Lennard Jones Kinetic diameter
See D W Breck "Zeolite Molecular Sieves"
Wiley Interscience 1974, p 636

Zeolite Nu-3 in appropriate cation form can be used to separate individual linear paraffins and olefins on a chain length basis, the components adsorbed can be varied by either varying cation content or temperature or both. Zeolite Nu-3 can also be used to separate linear paraffins and olefins from their mixtures or from iso-paraffins and iso-olefins or any branched chain or cyclic compounds.

Further applications include the separation of inert gases, or oxygen from nitrogen, and drying acid gas streams e.g. nitrogen oxides, sulphur oxides, sour natural gas.

In acid form, zeolite Nu-3 converts only linear alkanes or substituted alkanols of size close to 4.5 A and the products obtained are always linear with carbon number from 1 to 8, but mainly 2 to 6. Thus hydrogen Nu-3 can be used to convert methanol to olefins from $C_2$ to $C_8$, but largely $C_2$ to $C_4$ at 450° C.

The invention provides also a method of making zeolite Nu-3 which comprises reacting an aqueous mixture comprising at least one oxide $XO_2$, at least one oxide $Y_2O_3$ and at least one optionally substituted quinuclidinium ion.

Preferably the mixture has the molar composition:

$XO_2/Y_2O_3$: at least 5, preferably 10 to 300, especially 15 to 70;
$M^+/Q^+$: 0 to 2.0, preferably 0.2 to 0.8;
$H_2O/QZ$: 15 to 300, preferably 25 to 80;
$H_2O/XO_2$: 8 to 30, preferably 10 to 20;
$OH^-/XO_2$: 0.01 to 2.0, preferably 0.2 to 0.5;

where X is silicon and/or germanium, Y is one or more of aluminium, iron, or gallium, $M^+$ is an alkali metal ion, or mixtures of such ions which can include ammonium, and refers to free alkali, $Q^+$ is the aforesaid quinuclidinium ion or a precursor thereof, Z is hydroxide or is any acid radical capable of forming salts with the quinuclidinium ion, for example chloride, bromide or iodide and $OH^-$ refers to total free alkali provided by alkali metal, ammonium or any quaternary quinuclidinium compound or any combination of these. Whenever Z is an acid radical, at least an equivalent of free alkali must be employed to maintain the desired level of neutrality or alkalinity.

Suitable quinuclidinium ions include quinuclidinium ion itself and substituted quinuclidinium ions such as N-substituted derivatives (e.g. N-alkyl or N-hydroxyalkyl, preferably containing from 1 to 6 carbon atoms) and/or ring substituted derivatives (including, for example, one or more alkyl and/or hydroxyalkyl groups, preferably containing from 1 to 6 carbon atoms). The preferred quinuclidinium ion is the N-methyl quinuclidinium ion.

Suitable precursors include quinuclidine derivatives along with alcohols or alkylating agents e.g. alkyl halides such as methyl iodide, which can be added to the reaction mixture. Alternatively, such precursor reagents may be preheated together in a water-miscible solvent (e.g. methylethyl ketone) prior to the addition to the other reactants required for Nu-3 synthesis.

The preferred alkali metal (M) is sodium. The preferred oxide $XO_2$ is silica ($SiO_2$) and the preferred oxide $Y_2O_3$ is alumina ($Al_2O_3$).

The silica source can be any of those commonly considered for use in synthesising zeolites, for example powdered solid silica, silicic acid, colloidal silica or dissolved silica. Among the powdered silicas usable are precipitated silicas, especially those made by precipitation from an alkali metal silicate solution, such as the type known as "KS 300" made by AKZO, and similar products, aerosil silicas, fume silicas and silica gels suitably in grades for use in reinforcing pigments for rubber or silicone rubber. Colloidal silicas of various particle sizes may be used, for example 10-15 or 40-50 microns, as sold under the Registered Trade Marks "LUDOX", "NALCOAG" and "SYTON". The usable dissolved silicas include commercially available waterglass silicates containing 0.5 to 6.0, especially 2.0 to 4.0 mols of $SiO_2$ per mol of alkali metal oxide, "active" alkali metal silicates as defined in UK Pat. No. 1193254, and silicates made by dissolving silica in alkali metal hydroxide or quaternary hydroxide or a mixture thereof.

The alumina source is most conveniently sodium aluminate, but can be aluminium, an aluminium salt, for example the chloride, nitrate or sulphate, an aluminium alkoxide or alumina itself, which should preferably be in a hydrated or hydratable form such as colloidal alumina, pseudoboehmite, boehmite, gamma alumina or the alpha or beta trihydrate.

The reaction mixture is usually reacted under autogenous pressure, optionally with added gas, e.g. nitrogen, at a temperature from 85° to 250° C., preferably from 95° to 180° C., until crystals of zeolite Nu-3 form, which can be from 1 hour to many months, depending on the reactant composition and the operating temperature. Agitation is optional, but is preferable since it reduces the reaction time.

At the end of the reaction, the solid phase is collected on a filter and washed and is then ready for further steps such as drying, dehydration and ion-exchange.

If the product of the reaction contains alkali metal ions, these have to be at least partly removed in order to prepare the hydrogen form of Nu-3 and this can be done by ion exchange with an acid, especially a strong mineral acid such as hydrochloric acid or by way of the ammonium compound, made by ion exchange with a solution of an ammonium salt such as ammonium chloride. Ion exchange can be carried out by slurrying once or several times with the ion-exchange solution. The zeolite is usually calcined after ion-exchange but this may be effected before ion-exchange or during ion-exchange if the latter is carried out in a number of stages.

In general, the cation(s) of zeolite Nu-3 can be replaced by any cation(s) of metals, and particularly those in Groups IA, IB, IIA, IIB, III (including rare earths) VIII (including noble metals) and by lead, tin and bismuth. (The Periodic Table is as in "Abridgements of Specifications" published by the UK Patent Office). Exchange is carried out using any water soluble salts containing the appropriate cation.

When used as a catalyst, zeolite Nu-3 can be associated with an inorganic matrix, which can be either inert or catalytically active. The matrix may be present simply as a binding agent to hold the small zeolite particles (0.005 to 10 microns) together, or it may be added as a diluent to control the amount of conversion in a process which may otherwise proceed at too high a rate, leading to catalyst fouling as a result of excessive coke formation. Typical inorganic diluents include catalyst support materials such as alumina, silica, kaolinic clays, bentonites, montmorillonites, sepiolite, attapulgite, Fullers earth, synthetic porous materials such as $SiO_2$—$Al_2O_3$, $SiO_2$—$ZrO_2$, $SiO_2$—$ThO_2$, $SiO_2$—$BeO$, $SiO_2$—$TiO_2$ or any combination of these diluents. An effective way of mixing zeolite Nu-3 with such diluents is to mix appropriate aqueous slurries in a mixing nozzle and then to spray-dry the slurry. Other ways of mixing can be used.

If zeolite Nu-3 in any cationic form or as a catalytic composite is exchanged or impregnated with hydrogenation/dehydrogenation components, such as Ni, Co, Pt, Pd, Re, Rh, shape selective hydrocracking and reforming catalysts can be made, especially if the $Na_2O$ content is less than 0.1% w/w.

A wide range of shape selective hydrocarbon conversion catalysts can be prepared from zeolite Nu-3 by ion exchange or impregnation with cations, or oxides, selected from the following Cu, Ag, Mg, Ca, Sr, Zn, Cd, B, Al, Sn, Pb, V, P, Sb, Cr, Mo, W, Mn, Re, Fe, Co, Ni, nobel metals.

Usually the Nu-3 catalyst will be in acid form, thus stoichiometry is maintained by $H^+$ or $H_3O^+$ as an additional balancing cation, or as sole cation. Such catalysts may find application in the following processes; hydrodesulphurization, hydrodenitrification, catalytic dewaxing, selective alkylation of alkanes, dehydration reactions and oxidation.

The invention is illustrated by the following Examples.

EXAMPLE 1

Preparation of sodium N-methylquinuclidinium Nu-3

The synthesis mixture had the following molar composition 11.5 $Na_2O$, 17.1 QI, $Al_2O_3$, 60 $SiO_2$, 600 $H_2O$ 111 g of solid silica (AKZO KS 300—7.18 $Na_2O$, $Al_2O_3$, 695 $SiO_2$, 226 $H_2O$) were dispersed in 311.6 g of an aqueous solution containing 22 g sodium hydroxide and 5.6 g sodium aluminate (1.25 $Na_2O$, $Al_2O_3$, 3 $H_2O$). The resulting slurry was heated to 95° C. with stirring and then 120 g of N-methylquinuclidinium iodide were added with stirring. The resulting gel was reacted with stirring in a 1 liter stainless steel autoclave for 3 days at 180° C. The slurry product was filtered, washed twice with 1 liter of distilled water at 60° C., and then dried overnight at 120° C. The product was sodium N-methyl quinuclidinium Nu-3 having the X-ray diffraction data shown in Table 2, and a molar composition:

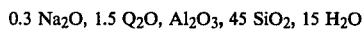
0.3 $Na_2O$, 1.5 $Q_2O$, $Al_2O_3$, 45 $SiO_2$, 15 $H_2O$

EXAMPLE 2

The product of Example 1 was calcined in air (saturated with water at 25° C.) for 48 hours at 450° C. The resulting sodium hydrogen Nu-3 had the X-ray data shown in Table 3. The calcined Nu-3 was slurry exchanged with 5 ml N.HCl per g of zeolite for 1 hour at 25° C. and was then washed twice with 10 ml distilled water per g of zeolite. Finally the product was dried overnight at 120° C. and then calcined at 450° C. in air for three hours. This hydrogen Nu-3 had identical X-ray data to sodium hydrogen Nu-3 and had the following molar composition ignoring hydrogen:

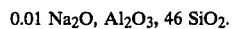
0.01 $Na_2O$, $Al_2O_3$, 46 $SiO_2$.

EXAMPLE 3

Preparation of sodium N-methylquinuclidinium Nu-3 with $SiO_2/Al_2O_3$ ratio 98

The synthesis mixture had the following molar composition:

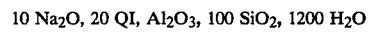
10 $Na_2O$, 20 QI, $Al_2O_3$, 100 $SiO_2$, 1200 $H_2O$ 163 g of KS300 silica were dispersed in 352.4 g of an aqueous solution containing 15.4 g sodium hydroxide and 5 g sodium aluminate. The slurry was heated to 95° C. with stirring and then 123 g of N-methylquinuclidinium iodide were added with stirring. The resulting gel was reacted with stirring in a 1 liter stainless steel autoclave for 3 days at 180° C. The slurry at the end of the run was treated in the same manner as in Example 1 and the product was found to be sodium N-methyl quinuclidinium Nu-3 of molar composition:

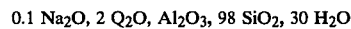
0.1 $Na_2O$, 2 $Q_2O$, $Al_2O_3$, 98 $SiO_2$, 30 $H_2O$

EXAMPLE 4

A sample of HNu-3 from Example 2 was tested as an acid catalyst in the dehydration of methanol. A catalyst of about 0.3 ml of 3 mm pellets was activated at 450° C. for 3 hours in a nitrogen stream. The catalyst was maintained at 450° C. and a sample of methanol (0.6 μl) was injected above the catalyst bed. The $C_1$–$C_4$ hydrocarbon analysis of the resulting products is given in Table 5. There was no significant production of aromatics.

TABLE 5

| | % v/v |
|---|---|
| methane | 19.8 |
| ethane | 0.6 |
| ethene | 22.7 |
| propane | 9.0 |
| propene | 38.6 |
| i-butane | <0.1 |
| n-butane | 0.4 |
| butene-2 | 2.4 |
| iso-butene | 2.9 |
| trans-butene-2 | 2.7 |
| cis butene-2 | 1.0 |

EXAMPLE 5

The synthesis mixture had the following molar composition:

19.5 $Na_2O$, 29 QI, $Al_2O_3$, 100 $SiO_2$, 1050 $H_2O$

The reaction was carried out as in Example 1, except that samples were taken after 3 days and 5 days. After 3 days the product was zeolite Nu-3, but after 5 days substantial recrystallisation of Nu-3 to α-quartz had occurred so that the final product contained about 70% α-quartz.

EXAMPLE 6

The synthesis mixture had the following molar composition:

5.85 $Na_2O$, 8.7 QI, $Al_2O_3$, 30 $SiO_2$, 315 $H_2O$ 131 g of KS 300 silica were dispersed in 427.6 g of an aqueous solution containing 15 g sodium aluminate and 23.6 g sodium hydroxide. The slurry was homogenised with stirring at 90° C. for 15 minutes, and then 146 g of N-methylquinuclidinium iodide were stirred in, and stirring was continued for 15 minutes. Finally the gel was transferred to a 1 liter, stirred, stainless steel autoclave, and was reacted for 5 days at 80° C. The slurry product was treated exactly as in Example 1. The dried zeolite Nu-3 product had the following molar composition:

0.96 $Na_2O$, 1.2 $Q_2O$, $Al_2O_3$, 20.8 $SiO_2$, 6.9 $H_2O$ and the X-ray data shown in Table 6.

EXAMPLE 7

The synthesis mixture had the following molar composition:

12 QI, 0.002 $Na_2O$, 9.8 $K_2O$, $Al_2O_3$, 50 $SiO_2$, 530 $H_2O$ 49 g potassium hydroxide and 27.4 g potassium aluminate (1.5 $K_2O$, $Al_2O_3$, 16 $H_2O$) were dissolved in 468 g water. Next, 160 g Degussa Aerosil 300 (0.145 $Na_2O$, $Al_2O_3$, 3000 $SiO_2$, 101 $H_2O$) were dispersed in the solution. The slurry was heated at 95° C. with stirring for 30 minutes, and then 160 g of N-methylquinuclidinium iodide were stirred in. The reaction was as in Example 1, except that the duration was 5 days at 180° C. The product was potassium N-methylquinuclidinium Nu-3 having the X-ray data shown in Table 7.

EXAMPLE 8

In this Example 11 g of the sodium hydroxide used in Example 1 were replaced by 41.3 g of caesium hydroxide. The reaction was exactly as Example 1 except that the reaction time was 7 days at 180° C. The product was sodium-caesium N-methylquinuclidinium Nu-3.

EXAMPLE 9

In this Example the 22 g of sodium hydroxide used in Example 1 were replaced by 13.2 g of lithium hydroxide, otherwise the reaction was as in Example 1. The product after 5 days at 180° C. was sodium, lithium, N-methylquinuclidinium Nu-3, having X-ray diffraction data as shown in Table 8.

TABLE 6

| X-RAY DATA FOR AS MADE ZEOLITE Nu-3 (EXAMPLE 6) | | | | | | |
|---|---|---|---|---|---|---|
| dA | 10.16 | 8.10 | 6.58 | 5.54 | 5.42 | 5.10 | 4.983 |
| 100I/Io | 5 | 31 | 21 | 10 | 6 | 77 | 12 |
| dA | 4.720 | 4.671 | 4.418 | 4.230 | 4.031 | 3.952 | 3.794 |
| 100I/Io | 12 | 10 | 5 | 57 | 100 | 9 | 36 |
| dA | 3.685 | 3.597 | 3.555 | 3.290 | 3.187 | 3.132 | 3.038 |
| 100I/Io | 4 | 5 | 6 | 18 | 6 | 50 | 10 |
| dA | 2.818 | 2.755 | 2.589 | 2.060 | 2.008 | 1.894 | 1.863 |
| 100I/Io | 6 | 36 | 10 | 6 | 3 | 4 | 3 |

TABLE 7

| X-RAY DATA FOR POTASSIUM Nu-3 (EXAMPLE 7) | | | | | | | | | | | |
|---|---|---|---|---|---|---|---|---|---|---|---|
| dA | 11.3 | 10.1 | 8.00 | 7.69 | 6.56 | 6.417 | 6.281 | 6.067 | 5.906 | 5.488 | 5.389 | 5.068 |
| 100I/Io | 7 | 6 | 31 | 6 | 23 | 4 | 6 | 2 | 1 | 13 | 5 | 82 |
| dA | 4.955 | 4.796 | 4.720 | 4.683 | 4.611 | 4.564 | 4.473 | 4.396 | 4.322 | 4.211 | 4.086 | 4.013 |
| 100I/Io | 17 | 4 | 10 | 12 | 24 | 8 | 8 | 9 | 9 | 59 | 12 | 100 |
| dA | 3.952 | 3.883 | 3.786 | 3.655 | 3.59 | 3.534 | 3.453 | 3.414 | 3.351 | 3.273 | 3.187 | 3.110 |
| 100I/Io | 9 | 8 | 38 | 12 | 8 | 16 | 5 | 4 | 13 | 22 | 9 | 49 |
| dA | 3.028 | 2.959 | 2.931 | 2.810 | 2.747 | 2.582 | 2.501 | 2.132 | 2.094 | 2.002 | 1.886 | 1.855 |
| 100I/Io | 9 | 2 | 3 | 5 | 36 | 8 | 6 | 5 | 5 | 3 | 4 | 3 |

TABLE 8

| X-RAY DATA FOR SODIUM, LITHIUM Nu-3 | | | | | | | | | | | |
|---|---|---|---|---|---|---|---|---|---|---|---|
| dA | 11.3 | 10.04 | 7.93 | 7.70 | 6.78 | 6.48 | 6.24 | 5.710 | 5.476 | 5.113 | 5.035 | |
| 100I/Io | 9 | 7 | 18 | 17 | 5 | 17 | 10 | 15 | 7 | 48 | 41 | |
| dA | 4.805 | 4.689 | 4.595 | 4.458 | 4.318 | 4.197 | 4.005 | 3.841 | 3.767 | 3.645 | 3.562 | |
| 100I/Io | 21 | 42 | 52 | 27 | 20 | 42 | 100 | 38 | 34 | 30 | 8 | |
| dA | 3.432 | 3.269 | 3.173 | 3.103 | 2.991 | 2.871 | 2.794 | 2.740 | 2.640 | 2.572 | 2.501 | |
| 100I/Io | 26 | 34 | 17 | 40 | 31 | 2 | 4 | 23 | 7 | 9 | 9 | |
| dA | 2.473 | 2.425 | 2.357 | 2.292 | 2.255 | 2.162 | 2.126 | 2.091 | 1.989 | 1.973 | 1.945 | 1.874 |

TABLE 8-continued
X-RAY DATA FOR SODIUM, LITHIUM Nu-3

| $100 I/Io$ | 5 | 4 | 5 | 4 | 3 | 2 | 3 | 4 | 3 | 3 | 2 | 7 |

EXAMPLE 10

A sample of H-Nu-3 from Example 2 was tested as an acid catalyst in the conversion of methanol. In a continuous flow apparatus, a bed of about 1 ml of H-Nu-3, particle size 500–700μ, was activated at 450° C. in air for 16 hours followed by 1 hour in nitrogen at 450° C. The catalyst was maintained at 450° C. and methanol vapour, 60% methanol 40% nitrogen was passed over the catalyst. The LHSV of methanol was 1.2 vol.feed/vol. catalyst hour. Analysis of $C_1$–$C_4$ hydrocarbons are given in Table 9. Methanol conversion was >95%. No liquid hydrocarbons were observed.

TABLE 9

| Time after start (min) | 3 | 33 | 64 | 95 |
|---|---|---|---|---|
| % v/v methane | 16.1 | 19.1 | 22.3 | 23.2 |
| ethane | 3.2 | 3.5 | 3.2 | 2.8 |
| ethene | 35.5 | 34.8 | 33.8 | 37.3 |
| propane | 3.2 | 3.5 | 3.2 | 1.1 |
| propene | 25.8 | 27.0 | 23.6 | 19.8 |
| butanes | 16.1 | 12.2 | 14.0 | 19.8 |
| Total $C_2$ + $C_3$ olefins | 61.3 | 61.8 | 57.4 | 57.1 |

EXAMPLE 11

Preparation of sodium N-methylquinuclidinium Nu-3 $SiO_2/Al_2O_3 = 43$

This sample of Nu-3 was prepared as in Example 1, except that the reaction was carried out for 5 days at 180° C. and the product contained about 18% α-quartz as an impurity. The hydrogen Nu-3 was prepared in the same way as for Example 2 except that the slurry exchange was carried out at 60° C. The hydrogen Nu-3 contained 18 times as much sodium as the catalyst of Example 2 and had the following molar composition, ignoring hydrogen:

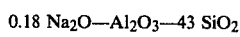

0.18 $Na_2O$—$Al_2O_3$—43 $SiO_2$

Conversion of Methanol

A sample of H-Nu-3 prepared in this Example was tested in the conversion of methanol. In a continuous flow reactor a bed of about 1 ml of H-Nu-3, particle size 500–700μ was activated at 450° C. in air for 16 hours followed by 1 hour in nitrogen at 450° C. The catalyst was maintained at 450° C. and 60% methanol in nitrogen was passed over the catalyst. The LHSV of methanol was 1.1 vol. feed/vol.catalyst/hour. Analysis of $C_1$–$C_4$ hydrocarbons are given in Table 10, no liquid hydrocarbons were observed. Methanol conversion was >95%.

TABLE 10

| Time from start (min) | 33 | 64 | 95 |
|---|---|---|---|
| % v/v methane | 15.9 | 20.2 | 21.7 |
| ethane | 3.2 | 4.7 | 3.1 |
| ethene | 34.1 | 35.7 | 43.4 |
| propane | 5.6 | 3.9 | 2.3 |
| propene | 29.4 | 22.5 | 17.1 |
| Butenes | 11.9 | 13.1 | 12.4 |
| Total $C_2$ + $C_3$ olefins | 63.5 | 58.2 | 60.5 |

EXAMPLE 12

A sample of the sodium N-methylquinuclidinium Nu-3 prepared in Example 6 was calcined in air for 72 hours at 450° C. The calcined Nu-3 was slurry exchanged with 10 ml N/1 HCl per g of zeolite for 1 hour at 60° C. and was then washed with 50 ml distilled water per g of zeolite. Finally, the product was dried overnight at 120° C. A sample of H-Nu-3 was tested as an acid catalyst in the conversion of methanol. In a continuous flow reactor about 1 ml of the catalyst, particle size 500–700μ was activated at 450° C. for 16 hours in air followed by 1 hour in nitrogen at 450° C. The temperature was maintained at 450° C. and 60% methanol in nitrogen was passed over the catalyst. The LHSV was 1.2 vol. feed/vol. catalyst/hour. Analysis of $C_1$–$C_4$ hydrocarbons are given in Table 11, no liquid hydrocarbons were observed. Methanol conversion was >90% in the first hour and about 50% in the second hour.

TABLE 11

| Time after start (min) | 32 | 64 | 95 |
|---|---|---|---|
| % v/v methane | 18.2 | 13.1 | 15.0 |
| ethane | 3.2 | 3.1 | 3.8 |
| ethene | 15.3 | 19.3 | 51.3 |
| propane | 5.6 | 2.5 | 1.3 |
| propene | 34.1 | 21.7 | 15.0 |
| Butenes | 23.6 | 31.1 | 13.8 |
| Total $C_2$ + $C_3$ olefins | 49.4 | 41.0 | 66.3 |

What we claim is:

1. Zeolite Nu-3 having a molar composition expressed by the formula:

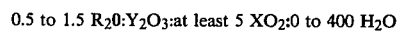

0.5 to 1.5 $R_2O:Y_2O_3$: at least 5 $XO_2$:0 to 400 $H_2O$ wherein R is a monovalent cation or 1/n of a cation of valency n where n is a whole number of 2 or more, X is silicon and/or germanium, Y is one or more of aluminium, iron or gallium and $H_2O$ is water of hydration additional to water notionally present when R is H, and having an X-ray diffraction pattern substantially as shown in Table 1.

2. Zeolite Nu-3 having a molar composition expressed by the formula:

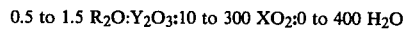

0.5 to 1.5 $R_2O:Y_2O_3$:10 to 300 $XO_2$:0 to 400 $H_2O$ wherein R is a monovalent cation of 1/n of a cation of valency n where n is a whole number of 2 or more, X is silicon and/or germanium, Y is one or more of aluminum, iron or gallium and $H_2O$ is water of hydration additional to water notionally present when R is H, and having an X-ray diffraction pattern substantially as shown in Table 1.

3. Zeolite Nu-3 according to claim 1 or claim 2 wherein the molar composition is such that there are from 0.8 to 1.5 moles of $R_2O$ per mole of $Y_2O_3$.

4. Zeolite Nu-3 according to claim 1 wherein R is or includes an alkali metal, ammonium or nitrogen-containing organic cation.

5. Zeolite Nu-3 according to claim 4 wherein the nitrogen-containing organic cation is an optionally substituted quinuclidinium ion, the X-ray diffraction pattern being as shown in Table 2.

6. Zeolite Nu-3 according to claim 5 which has been calcined, the X-ray diffraction pattern being as shown in Table 3.

7. Zeolite Nu-3 according to claim 1 as freshly made having a molar composition expressed by the formula:

0.3 to 1.2 $M_2O$:0.4 to 20 $Q$:$Y_2O_3$:5 to 1000 $XO_2$:0 to 400 $H_2O$ wherein M is an alkali metal or ammonium and Q is a nitrogen-containing organic cation.

8. A method of making zeolite Nu-3 as defined in claim 1 which comprises reacting an aqueous mixture comprising at least one oxide $XO_2$, at least one oxide $Y_2O_3$ and at least one oxide $R_2O$, the aqueous mixture comprising as $R_2O$ at least one optionally substituted quinuclidinium ion at a temperature in the range 85° to 250° C.

9. A method according to claim 8 wherein the aqueous mixture has the molar composition:
$XO_2/Y_2O_3$: at least 5
$M^+/Q^+$: 0 to 2.0
$H_2O/QZ$: 15 to 300
$H_2O/XO_2$: 8 to 30
$OH^-/XO_2$: 0.01 to 2.0
wherein X is silicon and/or germanium, Y is aluminium, iron or gallium, $M^+$ is an alkali metal or ammonium ion, $Q^+$ is an optionally substituted quinuclidinium ion, Z is hydroxide or an acid radical capable of forming salts with the quinuclidinium ion and $OH^-$ represents the total alkali provided by alkali metal, ammonium and quaternary quinuclidinium compound.

10. A method according to claim 9 wherein $Q^+$ is an N-methylquinuclidinium ion.

11. A method according to claim 9 or claim 10 wherein $XO_2/Y_2O_3$ is 10 to 300.

12. A method according to claim 11 wherein $XO_2/Y_2O_3$ is 15 to 70.

13. A method according to claim 9 wherein $M^+/Q^+$ is 0.2 to 0.8.

14. A method according to claim 9 wherein $H_2O/QZ$ is 25 to 80.

15. A method according to claim 9 wherein $H_2O/XO_2$ is 10 to 20.

16. A method according to claim 9 wherein $OH^-/XO_2$ is 0.2 to 0.5.

17. A method according to claim 8 conducted at a temperature in the range 95° to 180° C.

* * * * *